(12) United States Patent
Hohlbein et al.

(10) Patent No.: US 9,700,395 B2
(45) Date of Patent: Jul. 11, 2017

(54) DEVICE FOR IDENTIFYING ORAL CONDITIONS

(71) Applicant: COLGATE-PALMOLIVE COMPANY, New York, NY (US)

(72) Inventors: Douglas Hohlbein, Hopewell, NJ (US); Elizabeth Gittins, Stewartsville, NJ (US); Harsh M. Trivedi, Hillsborough, NJ (US); Sharon Kennedy, Randallstown, MD (US); Madhusudan Patel, Somerset, NJ (US); Deborah Peru, Lebanon, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 105 days.

(21) Appl. No.: 14/547,273

(22) Filed: Nov. 19, 2014

(65) Prior Publication Data

US 2015/0072301 A1  Mar. 12, 2015

Related U.S. Application Data

(63) Continuation of application No. 13/518,988, filed as application No. PCT/US2010/061708 on Dec. 22, 2010, now Pat. No. 8,920,746.

(Continued)

(51) Int. Cl.
*G01N 21/75* (2006.01)
*A61C 19/04* (2006.01)
(Continued)

(52) U.S. Cl.
CPC ............ *A61C 19/04* (2013.01); *A46B 11/001* (2013.01); *A46B 15/0002* (2013.01);
(Continued)

(58) Field of Classification Search
CPC ... A46B 11/001; A46B 15/0002; A46B 17/08; A46B 15/0055; A46B 2200/1066;
(Continued)

(56) References Cited

U.S. PATENT DOCUMENTS 2,154,209 A  4/1939  Kohn
4,538,631 A  9/1985  Prince
(Continued)

FOREIGN PATENT DOCUMENTS

EP  0097904  1/1984
JP  2003-250631 A  9/2003
(Continued)

OTHER PUBLICATIONS

Etienne et al., 2006, "Polyelectrolyte Multilayer Film Coating and Stability at the Surfaces of Oral Prosthesis Base Polymers: An in vitro and in vivo Study," J. Dental Research 85(1):44-48.
(Continued)

*Primary Examiner* — Dennis M White (57) ABSTRACT

The present invention relates to devices and systems for detecting the existence of oral conditions. In one aspect, the invention is a device including a detector capable of detecting a marker of an oral condition; a self-contained indicator that is actuated by a signal from the detector, wherein the indicator is one of a structural indicator adapted to undergo a physical change that is haptically perceptible, a dye adapted to be released into a user's mouth, and a flavor adapted to be released into a user's mouth; and wherein said device is detachably securable to an oral care implement.

15 Claims, 2 Drawing Sheets

Related U.S. Application Data (60) Provisional application No. 61/289,422, filed on Dec. 23, 2009.

(51) Int. Cl.

| | | |
|---|---|---|
| *A46B 11/00* | (2006.01) | |
| *A46B 15/00* | (2006.01) | |
| *A46B 17/08* | (2006.01) | |
| *A61B 10/00* | (2006.01) | |
| *A61C 15/02* | (2006.01) | |
| *A61C 19/06* | (2006.01) | |
| *G01N 33/543* | (2006.01) | |
| *A61K 6/00* | (2006.01) | |
| *A61C 17/00* | (2006.01) | |

(52) U.S. Cl.
CPC .......... *A46B 15/0055* (2013.01); *A46B 17/08* (2013.01); *A61B 10/0051* (2013.01); *A61C 15/02* (2013.01); *A61C 19/063* (2013.01); *G01N 33/5436* (2013.01); *G01N 33/54353* (2013.01); *A46B 2200/1066* (2013.01); *A61B 2010/0006* (2013.01); *A61C 17/005* (2013.01); *A61K 6/00* (2013.01); *A61K 6/0002* (2013.01)

(58) Field of Classification Search
CPC ........ A61B 10/0051; A61B 2010/0006; A61C 15/02; A61C 19/04; A61C 19/063; A61C 17/005; A61K 6/0002; A61K 6/00; G01N 33/5436; G01N 33/54353
See application file for complete search history.

(56) References Cited

U.S. PATENT DOCUMENTS

| | | | |
|---|---|---|---|
| 4,753,249 A | 6/1988 | Muller | |
| 5,000,193 A | 3/1991 | Heelis et al. | |
| 5,458,563 A | 10/1995 | Stewart | |
| 5,463,792 A | 11/1995 | Hogan et al. | |
| 5,578,023 A | 11/1996 | Schneider | |
| 5,842,248 A | 12/1998 | Van Grol et al. | |
| 5,910,122 A | 6/1999 | D'Angelo | |
| 6,048,735 A | 4/2000 | Hessel et al. | |
| 6,303,081 B1 | 10/2001 | Mink et al. | |
| 6,371,674 B1 | 4/2002 | Lerner | |
| 6,533,734 B1 | 3/2003 | Corley, III et al. | |
| 6,623,698 B2 | 9/2003 | Kuo | |
| 6,663,679 B1 | 12/2003 | Duncan | |
| 7,282,181 B2 | 10/2007 | Hudak et al. | |
| 7,449,001 B2 | 11/2008 | Stoltz | |
| 7,845,944 B2 | 12/2010 | DiGasbarro | |
| 7,883,724 B2 | 2/2011 | Konrad | |
| 8,092,110 B2 | 1/2012 | Russell et al. | |
| 8,636,433 B2 | 1/2014 | Lerner et al. | |
| 2003/0045814 A1 | 3/2003 | Sangha | |
| 2003/0053938 A1 | 3/2003 | Szeles | |
| 2003/0120180 A1 | 6/2003 | Kaylor et al. | |
| 2004/0005277 A1 | 1/2004 | Willison et al. | |
| 2004/0071594 A1 | 4/2004 | Malone et al. | |
| 2004/0082878 A1 | 4/2004 | Baldwin et al. | |
| 2004/0097834 A1 | 5/2004 | Stoltz | |
| 2004/0220498 A1 | 11/2004 | Li et al. | |
| 2005/0221401 A1 | 10/2005 | Nomura et al. | |
| 2005/0244794 A1 | 11/2005 | Kemp et al. | |
| 2006/0116561 A1 | 6/2006 | Tricca et al. | |
| 2006/0141421 A1 | 6/2006 | Braunecker et al. | |
| 2006/0225744 A1 | 10/2006 | Braunecker et al. | |
| 2006/0280650 A1 | 12/2006 | Wong et al. | |
| 2007/0151575 A1 | 7/2007 | De Masi, Sr. | |
| 2007/0173738 A1 | 7/2007 | Stoltz | |
| 2007/0255177 A1 | 11/2007 | Pronovost | |
| 2008/0060148 A1 | 3/2008 | Pinyayev et al. | |
| 2009/0012425 A1 | 1/2009 | Dodge et al. | |
| 2009/0293211 A1 | 12/2009 | Spungin | |
| 2009/0306543 A1 | 12/2009 | Slowey et al. | |
| 2010/0331725 A1 | 12/2010 | Libby et al. | |

FOREIGN PATENT DOCUMENTS

| | | |
|---|---|---|
| JP | 2004-108858 A | 4/2004 |
| JP | 2005-257604 A | 9/2005 |
| JP | 2009-216497 A | 9/2009 |
| KR | 2009-0090914 A | 8/2009 |
| WO | WO 2004/084752 | 10/2004 |
| WO | WO 2005/073721 | 8/2005 |
| WO | WO 2008/139324 | 11/2008 |
| WO | WO 2011/079164 | 6/2011 |

OTHER PUBLICATIONS

Green et al., 1999, *Protective Groups in Organic Synthesis*, New York, NY pp. 67-74 and 708-711.

International Search Report and Written Opinion in International Application No. PCT/US10/061704, mailed Apr. 19, 2011.

International Search Report and Written Opinion in International Application No. PCT/US10/061708, mailed Jul. 5, 2011.

International Search Report in International Application No. PCT/US09/054582, mailed Aug. 21, 2009.

Tangerman, 2002, "Halitosis in Medicine: A Review," International Dental J. 52(Supp. 3):201-206.

Written Opinion in International Application No. PCT/US10/061704, mailed Jan. 27, 2012.

DEVICE FOR IDENTIFYING ORAL CONDITIONS

CROSS REFERENCE TO RELATED APPLICATIONS

This application is a continuation of U.S. patent application Ser. No. 13/518,988, filed on Jun. 25, 2012, now allowed, which is a national stage entry under 35 U.S.C. §371 of International Patent Application No. PCT/US 2010/061708, filed on Dec. 22, 2010, which claims priority to U.S. Provisional Patent Application Ser. No. 61/289,422, filed on Dec. 23, 2009, the entireties of which are incorporated herein by reference.

BACKGROUND

Oral health problems can take many forms, such as tooth decay, periodontal disease, and bad breath. Bacteria play a major role in many oral health issues. For example, tooth decay and periodontal disease are often caused by undesirable bacteria in the mouth. Bacteria also interact with proteins present in saliva to form a film (plaque) that coats the teeth. If this plaque is not removed, acids produced by the bacteria can attack the teeth resulting in tooth decay. The plaque also may attack the soft gum tissue of the mouth leading to tooth loss in adults.

Oral care agents, such as rinses and mouthwashes, serve to remove bacteria and supply breath freshening agents. However, people do not always implement effective oral care procedures when using these liquids. Thus, significant amounts of harmful bacteria may remain in the mouth, attacking the teeth and gums, even after the person has completed his/her oral care routines.

Prior attempts at oral healthcare detection systems have not met with widespread adoption and have had limited functionality. For example, test strips employing conventional approaches for diagnosing the risk of dental caries using antibodies to detect the presence of oral bacteria have not achieved commercial success or widespread adoption by the public. Moreover, systems using color as an indicator of the presence of particular bacteria or enzymes have been burdened by the need for additional processing or apparatus, e.g., a colorimeter or fluorometer, to develop the color. In addition to the inconvenience of performing multiple steps, the use of additional agents and equipment may increase risk and increases cost.

Accordingly, it is desirable to provide a method and apparatus capable of overcoming the disadvantages described herein at least to some extent.

SUMMARY

In some embodiments, the present invention provides an oral device, comprising: a detector capable of detecting a marker of an oral condition; an agent capable of indicating the existence of an oral condition, wherein said agent is disposed within a releaser; and a releaser, configured to release said agent in response to a marker being detected by said detector.

Some embodiments provide an oral device, comprising: a detector capable of detecting a marker of an oral condition; a self-contained indicator disposed on a head of the oral device, wherein said indicator is actuated by a signal from the detector.

Further embodiments provide an oral system, comprising: an oral device configured for introduction into an oral cavity of a user; a detector capable of detecting a marker of an oral condition; an agent capable of indicating the existence of an oral condition, wherein said agent is disposed within a releaser; and a releaser, configured to release said agent in response to a marker being detected by said detector.

Other embodiments of the invention provide an oral system, comprising: an oral device, wherein said oral device comprises: a detector capable of detecting a marker of an oral condition; a self-contained indicator disposed on a head of the oral device, wherein said indicator is actuated by a signal from the detector.

In one embodiment the invention may be a device comprising: a detector capable of detecting a marker of an oral condition; a self-contained indicator that is actuated by a signal from the detector, wherein the indicator is one of a structural indicator adapted to undergo a physical change that is haptically perceptible, a dye adapted to be released into a user's mouth, and a flavor adapted to be released into a user's mouth; and wherein said device is detachably securable to an oral care implement.

In another embodiment the invention may be a device comprising: a detector capable of detecting a marker of an oral condition; a base comprising a structural indicator, wherein said structural indicator is one of: (1) a protrusion extending from the base; or (2) a pit formed into the base; wherein said detector is formed as a layer that is positioned atop of the base; and wherein said device is detachably securable to an oral care implement.

In yet another embodiment the invention may be a device comprising: a detector layer configured to detect a marker of an oral condition in an oral cavity of a user; an agent disposed within a releaser layer, wherein the releaser layer releases said agent into the oral cavity in response to detection of the marker, the agent configured to treat the oral condition; wherein the device is detachably securable to an oral care implement; and wherein the detector layer is positioned over the releaser layer and the agent.

DETAILED DESCRIPTION

As used herein, the term "self-contained" refers to a structure or component having—within itself—all that is necessary to carry out the desired function, without the need for additional processing, equipment or apparatus.

As used herein, the term "structural indicator" refers to an indicator whose physical change is visually and/or haptically perceptible.

Some embodiments provide an oral device that detects the oral condition of a user. In some embodiments, the device releases an agent in response to detecting the condition. In some embodiments, the condition may be an adverse condition, while in other embodiments the device indicates the user's good oral health. In some embodiments, the released agent is a dye or other indicator that may be released into the mouth or into a component that is sensed (for example seen, haptically sensed, smelled, or heard) by the user. In other embodiments, the released agent is a therapeutic agent effective in treating an adverse condition.

In some embodiments, the present invention provides an oral device, comprising: a detector capable of detecting a marker of an oral condition; an agent capable of indicating the existence of an oral condition, wherein said agent is disposed within a releaser; and a releaser, configured to release said agent in response to a marker being detected by said detector.

In some embodiments, the detector is a coating disposed on the releaser. In other embodiments, the detector is configured to dissolve in response to detecting the marker; and the dissolution of the detector induces the releaser to release the agent disposed therein. In further embodiments, the dissolution of the detector induces a physical change in the releaser. In some embodiments, the physical change is the creation of pores in the releaser. In other embodiments, the physical change is a shape change of the releaser.

In some embodiments, the dissolution of the detector induces a chemical change in the releaser. In some embodiments, the chemical change is the partial or complete dissolution of the releaser.

Other embodiments provide an oral device, comprising: a detector capable of detecting a marker of an oral condition; a self-contained indicator disposed on a head of the oral device, wherein said indicator is actuated by a signal from the detector.

In some embodiments, detection of a marker indicates good oral health. In some embodiments, the marker is selected from the group consisting of: triclosan; a phosphate; an amino acid; a potassium salt; and a stannous salt.

In other embodiments, detection of a marker indicates the existence of a disease, disorder or condition that is amenable to detection via examination of the oral cavity. In some embodiments, the marker is a bacterium, fungus, or virus. In some embodiments, the marker is selected from the group consisting of: C-reactive protein; glucose; cortisol; PSA; c-erbB-2 protein; a hormone; IL-1β, PGE2, arginine; gingipains; elastases; dipeptidylpeptidase; β-glucuronidase; lactoferrin; platelet-activating factor; ICPT; cathepsin B; cystatins; MMP-1; collagenase-2; MMP-8; MMP-13; MMP-9; hydroxyl-deoxyguanosine; an immunoglobulin; calprotectin; osteocalcin; ostenocetin; and osteopontin.

Some embodiments provide a device wherein the indicator is a dye. Other embodiments provide a device wherein the indicator is a structural indicator.

In some embodiments, the oral care implement is a toothbrush. In other embodiments, the oral care implement is an interdental pick.

In some embodiments, the device further comprises a replaceable cartridge, wherein the replaceable cartridge is detachably secured to the oral device; and wherein the replaceable cartridge comprises a detector, an agent, and a releaser. In some embodiments, the device further comprises a window disposed on the oral device to view the replaceable cartridge.

In some embodiments, the agent is exhausted after a single detection event. In some embodiments, the quantity of agent present in the releaser is sufficient for multiple detection events.

In some embodiments, the device further comprises a plurality of detectors, wherein at least two of the detectors are configured to detect different markers. In other embodiments, the device further comprises a plurality of agents, wherein at least two of the agents are capable of indicating the existence of different oral conditions.

Some embodiments provide a device further comprising: a plurality of releasers, each agent being disposed within a respective releaser of the plurality of releasers, each releaser being configured to release the respective agent in response to the respective marker being detected by the respective detector. In some embodiments, a first agent of the plurality of agents is available immediately upon detection of the respective marker; and a second agent of the plurality of agents is available after a delay following detection of the respective marker.

Some embodiments of the present invention provide an oral system, comprising: an oral device configured for introduction into an oral cavity of a user; a detector capable of detecting a marker of an oral condition; an agent capable of indicating the existence of an oral condition, wherein the agent is disposed within a releaser; and a releaser, configured to release an agent in response to a marker being detected by the detector.

In some embodiments, the oral system comprises an oral device, a detector capable of detecting a marker of an oral condition; a self-contained indicator disposed on a head of the oral device, wherein said indicator is actuated by a signal from the detector.

Figure 1:
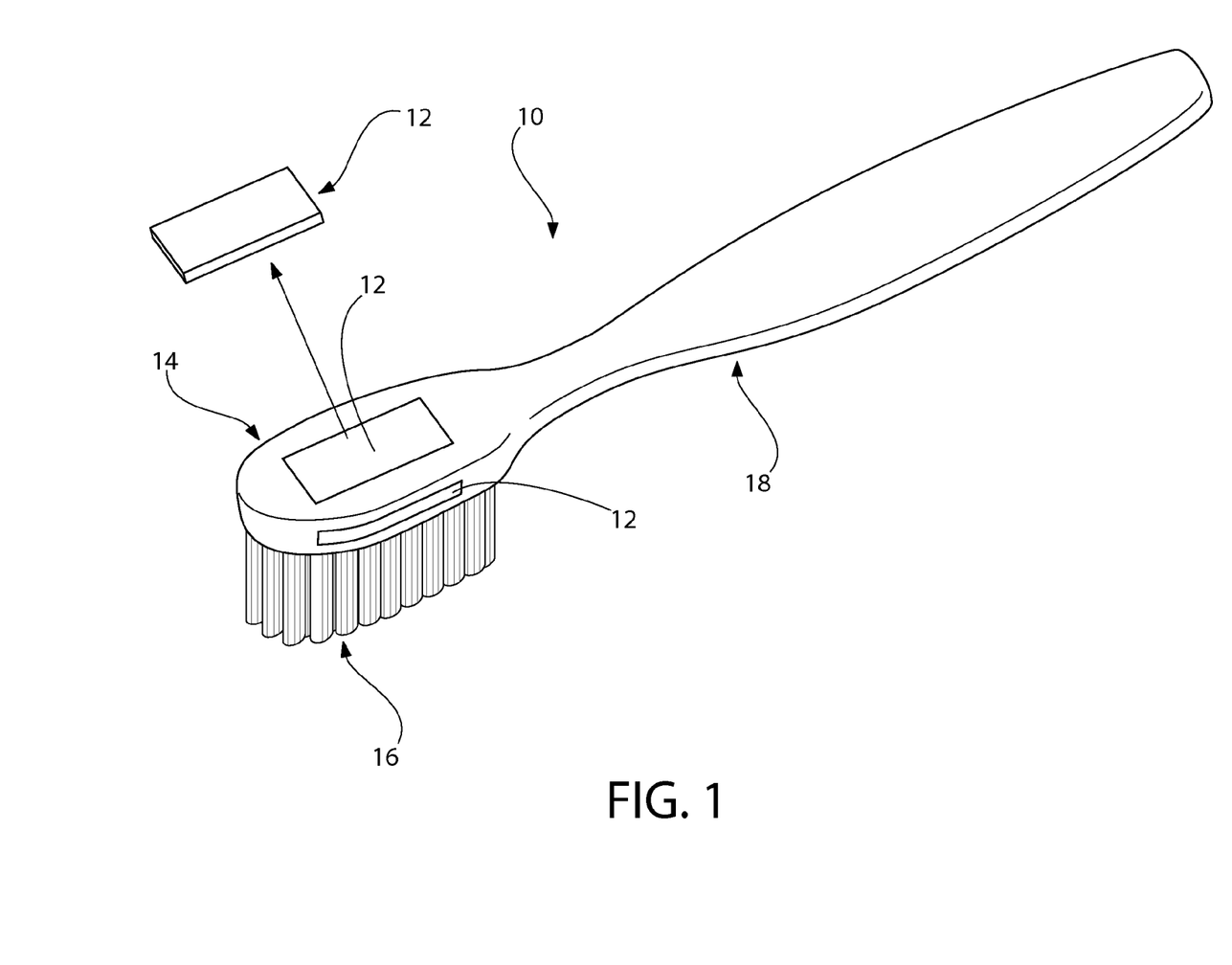
FIG. 1 is a perspective view of a device according to some embodiments of the invention.

As shown in FIG. 1, the device 12 may be disposed on an oral care implement. The device 12 may be disposed at any suitable location on the oral care implement 10. In the particular example shown, the oral care implement 10 is a tooth brush and the device 12 is disposed on a head 14 of the oral care implement 10. In some embodiments, the toothbrush is a manual toothbrush. In some embodiments, the toothbrush is an electric toothbrush. In some embodiments, the toothbrush is a powered toothbrush. In some embodiments, the toothbrush is a piezoelectric toothbrush. In some embodiments, the toothbrush is a vibratory toothbrush. In some embodiments, the toothbrush is a disposable toothbrush. Other embodiments provide a non-toothbrush oral care implement. Examples of suitable non-toothbrush oral care implements include, but are not limited to, interproximal or dental picks, floss, floss holding devices, tongue scrapers, and the like. In some embodiments, the device 12 is a replaceable cartridge. It is an advantage of embodiments of the invention that by incorporating the device 12 on the oral care implement 10, as depicted in FIG. 1, embodiments of the invention may be utilized without an added step or procedure to one's oral care regimen.

Alternatively, the oral care implement 10 may be a strip, such as a tooth whitening strip. In some embodiments, the device 12 may be embedded into a structure that fits over the user's tooth. For example, a brace, mouth-guard, denture, or other device designed for placement within the mouth or over one or more teeth for extended periods of time.

Although the device 12 is illustrated as being visible from the side of the head of the oral care implement 10, the invention is not limited to such an embodiment. For example, the oral care implement 10 may have a window on its back, side, handle, and/or shoulder, for viewing the indicator of the device 12. Thus, the color profile or "finger print" of the disease, diagnosis or progress of treatment displayed by the device 12 can be viewed through such a window on the oral care implement 10.

Figure 2:
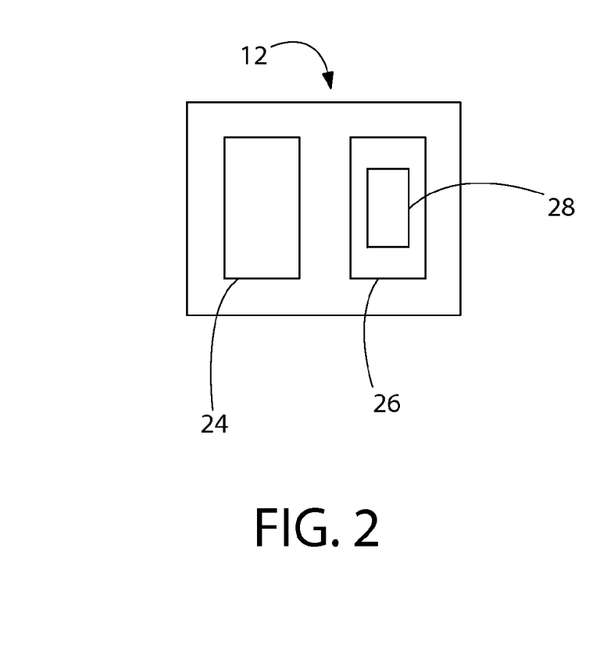
FIG. 2 is a block diagram of a device described herein.

FIG. 2 is a block diagram of the device 12 depicted in FIG. 1. As shown in FIG. 2, the device 12 includes a detector 24, a releaser 26, and an agent 28. In some embodiments, the detector 24 is configured to respond to a particular marker, trigger or stimulus that may be present in the oral cavity in such a way so as to induce the release of an agent 28 from the releaser 26. As described herein, some or all of the functionality of the detector 24, releaser 26, and agent 28 may be subsumed within the detector 24.

In some embodiments, the detector 24 is configured to detect any suitable marker or trigger in the saliva or air. The trigger may be a negative or positive indicator of oral hygiene or oral conditions. Examples of suitable markers/triggers include pH, atoms, molecules, proteins, organisms, oral activities such as triclosan, and the like. More specifically, suitable markers include phosphates, amino acids, potassium salts, and stannous salts. In some embodiments, the detector 24 is configured to detect a particular pH or range of pH.

In some embodiments, the releaser 26 is configured to release the agent 28 in any suitable manner. In some embodiments, the agent 28 is released within the device 12. In other embodiments, the agent 28 is released into the oral cavity. In some embodiments, the agent 28 is bound in a matrix of the releaser 26 and is released into the oral cavity environment as the releaser 26 dissolves in the presence of saliva. Optionally, the releaser 26 and detector 24 may be a single material configured to bind the agent 28 and release the agent 28 in response to the presence of a predetermined marker.

In some embodiments, the agent 28 may be released immediately after contact with the marker. In some embodiments, the agent 28 is released at predetermined time after contact between the detector 24 and the marker. In some embodiments, the agent 28 is released two (2) days after contact between the detector 24 and the marker. More particularly, suitable release periods include, for example, within 1, 2, 5, 10, 20, or 30 seconds, within 1, 5, 10, 15, 20, or 30 minutes, within 1, 2, 3, 5, or 10 hours, or within one or two days. These time periods are but examples and other periods of time are suitable as well.

In some embodiments, the agent 28 treats an oral condition. In some embodiments, the agent 28 serves as an indicator to the user that a condition is present. As described herein, the agent 28 may include any suitable drug or therapeutic agent, whitening agent or other active agent, dye or other indicator.

Figure 3:
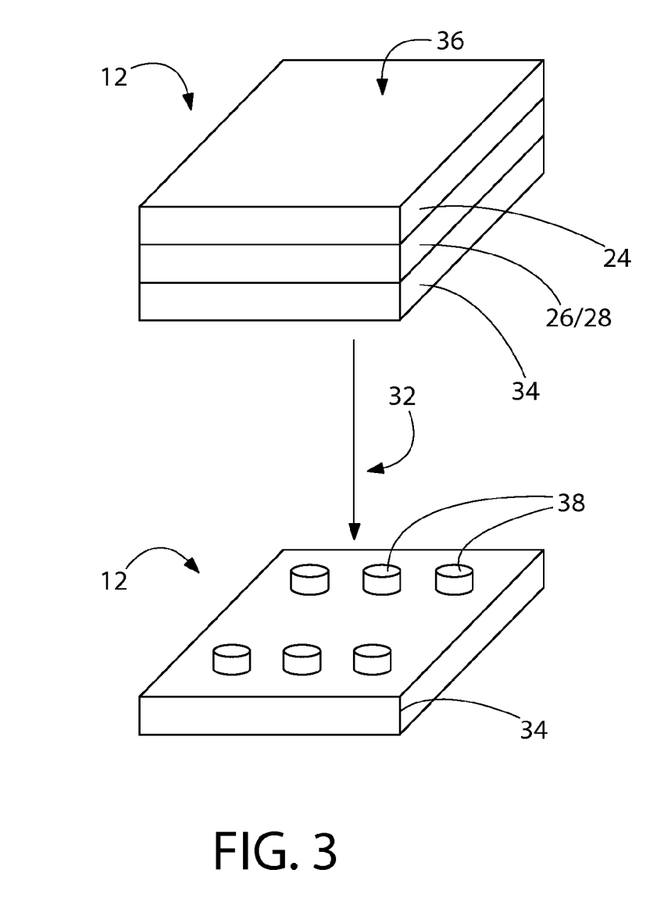
FIG. 3 is a schematic diagram of the device detecting a marker and releasing an agent in response to the detection event according to an embodiment of the invention.

As shown in FIG. 3, the device 12 is shown before and after exposure to a marker 32. Prior to exposure to the marker 32, the device 12 includes the detector 24 and releaser/agent 26/28 disposed upon a base 34. As illustrated in this example, the detector 24 and releaser/agent 26/28 may be configured as layers or membranes. When disposed in the oral care implement 10 (e.g., FIG. 1), the edges may be covered and, at least initially, only the top surface (e.g., the detector 24) may be exposed to the oral cavity environment. Optionally, the device 12 may include a protective membrane or cover 36. In some embodiments, the cover 36 is removable by the user prior to use. In some embodiments, the cover 36 is configured to provide additional protection to underlying layers. For example, the cover 36 may enable the user to decide a desirable time to utilize the device 12. In addition, the cover 36 may protect the device 12 during transportation and/or storage. For example, the cover 36 may prevent activation by air or moisture in the air.

In some embodiments, the detector 24 is configured to dissolve in response to the marker 32, and expose the releaser/agent 26/28 to the oral cavity environment. In response to exposure to the oral cavity environment, the releaser 26 is configured to dissolve and release the agent 28.

In some embodiments, the device 12 optionally includes one or more structural indicators 38. In general, the structural indicator 38 provides a visual or physical indication to the user that a particular marker is present. In some embodiments, the user-perceivable indication is light, a sound, a smell, a taste, a change in texture, or a vibration. In other embodiments, the indicator 38 is a protrusion extending out from the base 34. In some embodiments, the indicator 38 is a pit or ridge.

In some embodiments, contact between the detector 24 and the marker 32 induces a change in the physical or chemical structure of the detector 24. In some embodiments, this change is communicated, via a reactive functionality, to the releaser 26. In some embodiments, the releaser 26 undergoes a chemical or physical change which affects the shape and/or size of the releaser 26. In some embodiments, the change in the releaser 26 exposes the agent 28 to air and/or saliva. In some embodiments, the releaser 26 dissolves partially or completely, or the shape change may create pores in the releaser 26. In other embodiments, the change in the releaser 26 may cause the agent 28 to be expelled as a vapor into the oral cavity of the user.

The releaser 26 may be any suitable material that acts as a coating or containing material. For example the material may be a polymer such as a polymer film. The polymer may be nylons, polyethylenes, polypropylenes, hydroxypropylcelluloses, carbopols, silicas, elastomeric polymers, mixtures of polymers, gels and films, or combinations thereof. Suitable polymers are known in the art, including those described in Etienne O, et al. (Polyelectrolyte multilayer film coating and stability at the surfaces of oral prosthesis base polymers: an in vitro and in vivo study. J Dent. Res. 2006 January; 85(1):44-8), which is incorporated by reference herein in its entirety. In some embodiments, the material is an anti-microbial edible film, a protein or polypeptide sequence, viral capsule coats, micelles, vesicles, beads, strips, liposomes, water soluble food grade polymers, whey protein films, whey protein isolate coatings on polypropylene films, transglutaminase cross-linked gelatin films, edible cellulosic films and collagen.

The agent 28 may or may not be perceptible to the user immediately upon release from the device 12. In some embodiments, the agent 28 is contained within a second protective coating such as the cover 36. The cover 36 may be selected to have any desired properties. For example, dissolution of the second coating may require the continued presence of the marker and a second shape change. The cover 36 may also dissolve slowly in the mouth in response to saliva. The agent 28 may be released during or after dissolution of the second coating. Control over the stage at which the agent 28 becomes active in the oral cavity allows targeted release of the agent 28 to particular parts of the body. For example, if the user has a gingivitis that is signaled by an increase in the amount of collagenase, as the cover 36 dissolves, the agent 28 in the form of an active compound such as cetylpyridinium chloride, chlorohexidine or other active compound that is configured to be released to treat the oral disease or ailment. Naturally other actives/drugs could be used in a similar manner. The device 12 may contain different agents such that immediate and extended release formulations of a particular agent can be delivered from the same device 12.

Any suitable reactive functionality may be used to connect the detector 24 to the releaser 26.

In some embodiments, the oral conditions identified by the devices described herein include, but are not limited to, conditions associated with poor oral care, conditions which may be diagnosed by examination of the oral cavity, and systemic conditions which have been recognized or otherwise identified by the American Dental Association to be correlated with poor oral care.

Oral diseases suitable for detection include caries, gingivitis, periodontitis, halitosis and dry mouth. Gingivitis may be indicated by the markers IL-1β, PGE2, arginine and Gingipains. Gingivitis may also be indicated by elevated levels of one or more of *P. gingivalis, C. gingivalis, P. melaninogenica, Treponema denticola, Bacterioides forsythus* and *S. mitis*. Halitosis may be indicated by volatile sulfur compounds, including methyl mercaptan, dimethylsulfide and hydrogen sulfide. Periodontitis may be indicated by elastases, dipeptidylpeptidase, β-glucuronidase, lactoferrin, platelet-activating factor (PAF), ICPT (pyridinoline cross-linked carboxyterminal telopeptide), cathepsin B (a cysteine protease), cystatins, MMP-1, collagenase-2 (matrix metalloproteinase, MMP-8), MMP-13 (collagenase-3), gelatinase (MMP-9), hydroxyl-deoxyguanosine and immunoglobulins such as IgA, IgG and IgM. Bone-related biomarkers from oral fluids associated with periodontal diseases also include calprotectin, osteocalcin, ostenocetin and osteopontin.

Caries may be indicated by low salival pH, local pH (i.e at specific locations on the hard tissue) and by acid-producing oral bacteria (specifically *Lactobacillus* species, *Streptococcus mutans*, and *Actinomyces* species). A few non-oral based systemic diseases that are also indicative with oral malodor are: fetor hepaticus, an example of a rare type of bad breath caused by chronic liver failure; lower respiratory tract infections (bronchial and lung infections); renal infections and renal failure; and trimethylaminuria ("fish odor syndrome") (Tangerman A. Halitosis in medicine: a review. *Int Dent J.* 2002 June; 52 Suppl. 3:201-6), which is incorporated by reference herein in its entirety. High concentrations of acetone (known as "acetone breath") in breath can indicate diabetic ketoacidosis.

The marker 32 may also be a protein, lipid, glycoprotein, or carbohydrate. For example, inflammation markers may be cytokines, metalloproteases, or prostaglandins such as PGE2. Cytokines useful for diagnosis include: IL-6, IL-1β, IL-8, IL-10, IL-12, TNF-α, RANKL.

In some aspects, the marker 32 may be detected in exhaled gases. For example. bacterial metabolite markers may be used to indicate the presence of bacteria, as an indication of bad breath. Bacteria metabolite markers includes amine containing compounds such as trimethylamines and sulfur-containing compounds identified by the term Volatile Sulfur Compounds (VSC's) as well as beta-galactosidase activity. Other volatile compounds that contribute to halitosis include volatile short-chain fatty acids, polyamines, alcohols, phenyl compounds, alkanes, ketones, and nitrogen-containing compounds.

In some embodiments, the agent 28 is released in response to one or more detected markers. In some embodiments, the agent 28 is an abrasive, mouth freshener, teeth whitening agent, vitamin, anti-oxidant, buffering agent, prebiotic, antibacterial/anti-microbial agent, de-sensitizing agent for the mouth and teeth, anti-cavity agent, or anti-inflammatory agent.

In some embodiments, the device 12 is able to detect a lack of fluid within the mouth, and release a stimulant for the salivary gland. The amount and rate of delivery for the agent 28 will depend on the amount needed and the agent 28 being applied.

An anti-plaque agent 28 may also be released in response to detection of plaque and/or plaque-forming conditions. Any suitable anti-plaque agent may be used. For example, the agent 28 may be enzymes such as proteases (neutral, acidic, and basic proteases), mucinases, pancreatin, fungal enzymes, amylases, dextranase, moimnase, amyloglucosidase, glucose oxidase, cellulase, α-glucanase, α-amylase, cutinase, amyloglucosidase, glucosidase, lactoperoxidase and mixtures thereof.

The agent 28 may comprise a dye. Ideally, the dye will be used in sufficient amount to provide a visually observable color change. The degree of color intensity can be correlated with severity or prevalence of disease or disorder.

Dyes can include for example, azo dyes, porphyrins, porphines, indigos, triarylmethanes, fluoresceins, chlorophylls and their metal such as copper complexes, iron salts, polyphenols, pthalocyanines, anthocyanins, vitamins, benikoji, tumeric and its extracts, inorganic based dyes and fluorescent or phosphorant dyes such as quantum dots. Suitable dyes may also include tartrazine, amaranath, allura red, erythrosin B, indigo carmine, brilliant blue FCF, beta-carotene, fast green FCF, erioglaucine disodium salt, curcumin, chromotrope FB, new coccine, riboflavin 5'monophosphate sodium salt, riboflavin, betanin, lycopene, chocolate brown HT, brilliant black BN, green S, indogtine, bixin, brilliant scarlet 4R, amaranath, carmoisine azorubine, cochineal and sunset yellow FCF.

Detection of disease or disorder is signaled from about 1 second to about 36 hours after detection of the analyte or marker, or after cleavage or degradation of the releaser 26. More specifically, detection of disease or disorder is signaled from about 1 second to about 120 seconds after use.

It is an advantage of embodiments of the invention that having a protective coating, such as the cover 36, that wears away over a set period of time (e.g., 4 weeks) allows the device 12 to have a second functionality. The cover 36 may be configured to slowly dissolve after a predetermined period of use to expose the detector 24 and/or releaser/agent 26/28. In certain embodiments, the user is able to evaluate improvement in their oral care regimen.

EXAMPLES

Example 1

The releaser 26 includes a polymer containing a cleavable ester bond covalently bound to erythrosine B. The polymer is shaped and securely fitted into the back of a toothbrush head using food-grade adhesive. Upon brushing, and presence of a diagnostic esterase in the oral cavity, the ester bond is cleaved, releasing the dye into the membrane, which signals a color change on the oral care implement 10. In a particular example, this color change is viewable on back of the head 14, as shown in FIG. 1.

Alternatively, the agent 28 can be released into back of the head 14. The release of the agent 28 may aid in the breakdown of the releaser 26 which would signal a shape change to the user. The diagnostic ester may be formed by reacting a hydroxy-terminated polymer with a dye possessing an acid functional group such as erythrosin B. Upon detection of the esterase, the ester is cleaved, releasing the colored dye. The ester can be formed by any means known to those skilled in the art. To increase the signal strength of detection to at least fourfold one could attach the dye via a biotin or strepavidin moiety.

Example 2

The agent 28 may be tethered to the releaser 26. For example, triclosan could be tethered to an acid terminated polymeric membrane via one of its phenol groups. This coupling would form the necessary diagnostic cleavable ester. Upon detecting esterase activity in the oral cavity, the triclosan is configured to be released into the oral cavity. The amount of triclosan is optionally about 0.3% weight to volume (w/v) of the agent 28. The releaser 26 may also contain polymers that are directly attached to one or more dyes. For example, both triclosan and a dye are attached to the releaser 26. In this manner, the same toothbrush is configured to signal the presence of enzyme activity through color or shape change on the back of the toothbrush but may also treat the condition by releasing triclosan into the oral cavity.

In one embodiment, the releaser 26 possesses discrete segments of detectors or enzyme cleavable groups. For example, the outer edges of the releaser 26 possess few detectors while the center of the releaser 26 possesses up to ten (10) fold more. Recognition and cleavage of the enzyme substrate in the center of the releaser 26 will provide a distinct visual shape change upon detection of the enzyme. Polymers arranged linearly or radially could offer different shape changes upon detection of a marker 32.

Example 3

In this example, the agent 28 is embedded or trapped in a mesh of the diagnostic releaser 26 attached to the tip of an interdental stick. The releaser 26 is made of collagen and contained inside the releaser 26 is a highly concentrated flavor and/or dye. Upon use of the interdental stick near the gumline, the device 12 is configured to detect the presence of gingivitis. In response to detecting gingivitis, the device 12 is configured to release matrix metallopeptidase 8 (MMP-8) into the gum pocket and oral cavity. This breaks down the collagen matrix of the releaser 26, thereby inducing release of the diagnostic flavor. The dye may be visualized in the matrix itself or may be released into the oral cavity for further oral feedback to the user. Break down of the releaser 26 and release of dye may be viewed also as a shape change in the releaser 26. The oral care implement 10 may have a handle and a head designed for temporary placement in the oral cavity along the gum area. Alternatively, the oral care implement 10 may be in a form useful for extended placement in the mouth, such as a strip. An example of a collagen containing membrane is illustrated in Table 1 (below):

TABLE 1

| Ingredient Name | Example |
|---|---|
| Collagen | 90.0% |
| Flavor | 9.0% |
| FD&C No. 1 | 1.0% |
| Total Materials | 100% |

Example 4

Beta-galactosidase activity has been associated with organoleptic scores for whole mouth and tongue malodor. In this example, the end of the oral care implement 10, such as a single use toothbrush, contains the releaser 26 that could indicate bad breath. The end of the oral care implement 10 may be utilized, first to test if the person has bad breath, and if bad breath is detected, the oral care implement 10 is configured to provide a visual indicator of the bad breath to inform the user. In response, the user may elect to utilize a breath freshening bead present in the oral care implement 10 to freshen their breath. In this embodiment, the releaser 26 may include a dye such as fluorescein or a unpleasant flavor attached to beta-D-galactose. Upon detection of beta-galactosidase in saliva or gingival crevicular fluid, the glycosidic bond between the membrane and fluorescein or unpleasant flavor is configured to loose structural integrity—releasing the dye or unpleasant flavor into the oral cavity. The user, so informed, may then elect to freshen or treat their breath by brushing, for example.

Example 5

The end of the oral care implement 10 is configured to include an interdental tip shape. The interdental tip includes a diagnostic, acid-sensitive polymer. Upon use and presence of a harmful acid environment, the tip is configured to change color. Brushing with COLGATE® Enamel Strengthening toothpaste would reduce the acid environment and thereby protect the teeth from further erosion. A new interdental tip can be inserted on the end of the oral care implement 10 to verify the new acid free oral environment.

Low salival pH or local pH (e.g., at specific locations on the hard tissue) could be detected using a releaser 26 that is pH sensitive. The acid sensitivity of the detector 24 could be tuned to lie between pH 3 to 14. For detection of enamel erosion, where low local pH is a causative agent and where if untreated can lead to cavities and periodontitis, the releaser 26 could be sensitive to pH less than 5.5, the critical pH for demineralization of teeth. Rapid breakdown of the releaser 26 could occur at lower pH values such as 2 to 4.

There are many available acid-sensitive functional groups that could be incorporated into the releaser 26 and calibrated to desired pHs. Acid-protecting groups include acetals or ketals. Additional examples can be found in T. W. Green, P. G. M. Wuts, Protective Groups in Organic Synthesis, Wiley-Interscience, New York, 1999, 67-74, 708-711.

In one example, the phenol groups of azo dyes could be protected with an acid labile protecting group such as a tert-butyl group or tetrahydropyranyl group. Upon acid detection, the protecting group could be cleaved restoring the conjugated system of the azo dye and its original visible color.

In another embodiment, pH sensitive cross-linking groups (for example, carbonate) could be attached between the dye and/or treatment active and the releaser 26. Cleavage of the group upon desired local or saliva pH separates the dye and/or treatment active from the releaser 26. The agent 28 could be attached to the releaser 26 by methods known to those skilled in the art. They could, for example, be linked via peptide, urethane, carbonate, hydrazide or carbon-carbon based linkages.

In another embodiment, the detector 24 may include a pH sensitive moiety such as a titratable polymer. The acid sensitive polymer may be alkylacrylic acid based such as polymethylacrylic acid, polyethylacrylic acid, polypropylacrylic acid and polybutylacrylic acid. The polymer could be present at mol % of between 0.01-100%, depending on amount of dye or agent 28 present. In another example, the releaser 26 may include dyes trapped or doped into different acid-sensitive materials that could be released upon degradation of the acid-sensitive material.

In another embodiment, an acid sensitive dye such as erythrosine B or Oregon Green 488 could be tethered onto the releaser 26 through either hydroxyl, carboxy, amine, thiol, hydrazide, isothiocyanate or any other suitable cross-linking group. These dyes are configured to change color upon acid detection. The entire releaser 26 need not be comprised of these dye tethered polymers. The dyes may be doped to a percent weight to provide a visually observable color change on the releaser 26. The percent weight of dye to releaser 26 may range between 0.0001-100%, optionally, 0.001% and at most 20% by weight of the releaser 26.

In another embodiment, the acid-sensitive molecule breaks down and reacts with an imbedded molecule to create a color that could be visually detected.

Example 6

Oral bacteria, *Treponema denticola, Porphyromonas gingivalis*, and *Bacteroides forsythus* are three anaerobic bacteria highly associated with adult periodontitis and malodor. All three bacteria release a distinctive enzyme that can break down the synthetic peptide benzoyl-DL-arginine-naphthylamide (known as BANA) into beta-naphthylamide. The detector 24 is configured to include a polymer containing for example, benzoyl-DL-arginine-naphthylamide groups. Detection and subsequent breakage of diagnostic bond will unravel and break down the releaser 26 releasing the dye or agent 28 imbedded within it. Unlike the BANA test, in this invention there is no need to incubate the by-product beta-naphthylamide for 5 min at 50° C. with an azo dye to see a chromagenic response since there would be a high concentration of the diagnostic cleavable peptide sequence directly bound to the dye. The high concentration of the dye is readily visible by the consumer. Also, enzymes are very efficient and work best at 37° C., the temperature inside the oral cavity.

The releaser 26 or polymer containing the diagnostic synthetic peptide sequence could be covalently bound to a diagnostic dye, erythrosine B. The polymer could be shaped and securely fitted into the strip present on a tongue scrapper using food adhesive. Upon use, the presence of the three malodor causing bacteria oral cavity, would be signaled by release of the color into the strip and presence of the agent 28 that can breakdown the strip further, thus appearing as a shape change to the consumer.

Example 7

Receptors for hormones such as cortisol, progesterone, testosterone and endorphins can be bounded covalently or non-covalently to the releaser 26 that forms part of a spring-load release catch mechanism. Binding of the hormone to its receptor on the spring, releases the spring, opening a pore or gate to rapidly release the colored dye for hormone detection. The spring loaded release mechanism ensures rapid ejection of the dye from the membrane. The spring loaded/cantilever method can be applied broadly to all markers. The receptors need not be covalently bound to a colored dye. In this example, the spring loaded and released method is a label-free method in that neither the analyte nor receptor need to be labeled for detection of the marker 32.

The many features and advantages of the invention are apparent from the foregoing disclosure, and thus, it is intended by the appended claims to cover all such features and advantages of the invention that fall within the true spirit and scope of the invention. Further, since numerous modifications and variations will readily occur to those skilled in the art, it is not desired to limit the invention to the exact construction and operation illustrated and described, and accordingly, all suitable modifications and equivalents will necessarily fall within the scope of the inventions described herein.

What is claimed is:

1. A device comprising:
  a detector capable of detecting a marker of an oral condition;
  a self-contained indicator that is exposed by the detector, wherein the indicator is a structural indicator adapted to undergo a physical change that is haptically perceptible;
  a base comprising the indicator, wherein said indicator is the structural indicator and the structural indicator is one of: (1) a protrusion extending from the base; and (2) a pit formed into the base;
  wherein said detector is formed as a layer that is positioned atop of the base;
  wherein said indicator is exposed by the detector; and
  wherein said device is detachably securable to an oral care implement.

2. The device of claim 1, wherein detection of said marker indicates good oral health.

3. The device of claim 2, wherein said marker is selected from the group consisting of: triclosan; a phosphate; an amino acid; a potassium salt; and a stannous salt.

4. The device of claim 1, wherein detection of said marker indicates the existence of a disease, disorder, or condition that is amenable to detection via examination of the oral cavity.

5. The device of claim 4, wherein said marker is a bacteria, fungi, yeast or virus.

6. The device of claim 4, wherein said marker is selected from the group consisting of: C-reactive protein; glucose; cortisol; PSA; c-erbB-2 protein; a hormone; IL-1β, PGE2, arginine; gingipains; elastases; dipeptidylpeptidase; β-glucuronidase; lactoferrin; platelet-activating factor; ICPT; cathepsin B; cystatins; MMP-1; collagenase-2; MMP-8; MMP-13; MMP-9; hydroxyl-deoxyguanosine; an immunoglobulin; calprotectin; osteocalcin; ostenocetin; and osteopontin.

7. The device of claim 1, wherein the oral care implement is a toothbrush comprising a handle and a head, the head having a front surface and an opposing rear surface.

8. The device of claim 7 further comprising a plurality of tooth cleaning elements extending from the front surface of the head, and wherein the device is coupled to the rear surface of the head.

9. The device of claim 1, wherein the detector has a smooth outer surface.

10. The device of claim 1, wherein the detector encapsulates the structural indicator.

11. The device of claim 1, wherein the detector is configured to dissolve in response to detecting the marker; and wherein the dissolution of the detector exposes the structural indicator.

12. The device of claim 1, wherein the detector has a thickness which is not constant.

13. The device of claim 1, wherein the oral care implement is a toothbrush comprising a handle and a head, the head having a front surface and an opposing rear surface;
  wherein the toothbrush comprises a plurality of tooth cleaning elements extending from the front surface of the head; and
  wherein the base and the detector collectively form a unitary structure that is coupled to the rear surface of the head.

14. The device of claim 1 further comprising:
  a releaser having an agent disposed therein; and
  wherein said releaser and said agent are formed together as a second layer, the second layer being positioned between the base and the detector.

15. The device of claim 14 further comprising a cover that forms a third layer, the cover positioned atop of the detector.

* * * * *